(12) United States Patent
Bell et al.

(10) Patent No.: US 7,144,294 B2
(45) Date of Patent: *Dec. 5, 2006

(54) COMPRESSION GARMENT (75) Inventors: Lesli R. Bell, Williston, VT (US); Eugenie Z. Lindahl, Colchester, VT (US)

(73) Assignee: Lightning2 LLC, Williston, VT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/200,214

(22) Filed: Aug. 9, 2005

(65) Prior Publication Data

US 2006/0019576 A1    Jan. 26, 2006

Related U.S. Application Data

(63) Continuation of application No. 10/187,164, filed on Jul. 1, 2003, now Pat. No. 6,860,789.

(51) Int. Cl.
*A41C 3/02* (2006.01)
*A61F 5/03* (2006.01)

(52) U.S. Cl. .................. 450/20; 450/1; 450/8; 450/17; 450/75; 2/102; 2/109; 602/53; 602/61

(58) Field of Classification Search .......... 2/102, 2/463, 67, 73, 69, 104–106, 109, 110, 114, 2/113; 450/5, 8, 10, 11, 9, 3, 4, 7, 15, 16, 450/17, 20, 21, 25, 30, 31, 26, 28, 34, 65, 450/66, 75–79, 70, 58, 60; 602/75, 41, 76, 602/19, 61, 53; 128/874, 101.1, 873, 845, 128/99.1, 846

See application file for complete search history.

(56) References Cited

U.S. PATENT DOCUMENTS 1,063,399 A    6/1913   Stansbury 1,254,043 A    1/1918   James ................ 450/31

(Continued)

FOREIGN PATENT DOCUMENTS

FR    958.747    9/1949

(Continued)

OTHER PUBLICATIONS www.fourgates.com/clthngstretchbra.asp, Mar. 11, 2002.
www.thebraladies.com/bras.html, Sep. 4, 2001.

(Continued)

*Primary Examiner*—Amy B. Vanatta
(74) *Attorney, Agent, or Firm*—Downs Rachlin Martin PLLC (57) ABSTRACT

A garment (1) for providing compressive forces to a torso to help eliminate or reduce swelling caused by an accumulation of lymph fluid in the torso region. An embodiment of the present invention includes an outer covering (10) of compression fabric, wide shoulder straps (22, 24), front and back panels of compression fabric (12, 14, 16, 18), a non-rolling rib band (72), axilla gussets (82, 84), and both front closure (40) and back closure (50). The garment may also include one or more princess seams (102, 104, 102', 104') so as to enable the front panel(s) to encapsulate and hold the user's breasts in place at the same time that compressive forces are applied, as well as one or more front shelves (132, 134) in the front panel(s) for providing upward compressive support to the breast tissue, thereby holding the tissue in a proper neutral position so that inward compressive forces acting on the tissue provide maximum effect. Through the use of the present invention, a user can provide the proper amount of compressive support that is required for each area of the torso. To wit, the user can set the adjustable closure to a desired tightness and provide up to four different levels of support over the torso region.

47 Claims, 6 Drawing Sheets

U.S. PATENT DOCUMENTS

| | | | | |
|---|---|---|---|---|
| 2,436,430 | A | 2/1948 | Hart | 2/42 |
| 2,471,670 | A | 5/1949 | Becker et al. | 450/5 |
| 2,864,373 | A | 12/1958 | Buckley | 128/481 |
| 2,888,930 | A | 6/1959 | Coleman et al. | 128/429 |
| 3,020,914 | A | 2/1962 | Garson | 450/20 |
| 3,093,137 | A | 6/1963 | Dugan | 450/19 |
| 3,173,420 | A | 3/1965 | Mazzoni et al. | 128/478 |
| 3,208,453 | A | 9/1965 | Cole | 450/4 |
| 3,436,762 | A | 4/1969 | Cahan | 2/67 |
| 3,718,143 | A | 2/1973 | Pagano et al. | 450/75 |
| 3,950,792 | A | 4/1976 | Williams | 3/36 |
| 4,398,538 | A | 8/1983 | Johnson | 450/8 |
| 4,440,174 | A | 4/1984 | Cordova | 128/455 |
| 4,538,614 | A | 9/1985 | Henderson | 450/70 |
| 4,630,610 | A | 12/1986 | Fletcher | 450/77 |
| 4,804,351 | A | 2/1989 | Raml et al. | 450/58 |
| 4,916,755 | A | 4/1990 | Feigenbaum et al. | 2/67 |
| 5,033,986 | A | 7/1991 | Feigenbaum et al. | 450/30 |
| 5,152,741 | A | 10/1992 | Farnio | 602/79 |
| 5,158,541 | A | 10/1992 | McCurley | 602/79 |
| 5,257,956 | A | 11/1993 | Ewen | 450/1 |
| 5,359,732 | A | 11/1994 | Waldman et al. | 2/67 |
| 5,427,563 | A | 6/1995 | Manning | 450/79 |
| 5,429,593 | A | 7/1995 | Matory | 602/79 |
| 5,690,537 | A | 11/1997 | Kalmus | 450/57 |
| 5,800,245 | A | 9/1998 | Barbe-Vicuna et al. | 450/57 |
| 5,820,444 | A | 10/1998 | McGaughey | 450/70 |
| 5,839,942 | A | 11/1998 | Miller | 450/58 |
| 5,868,601 | A | 2/1999 | Kelemencky | 450/59 |
| 5,946,726 | A | 9/1999 | Green | 2/109 |
| 5,950,238 | A | 9/1999 | Klein | 2/69 |
| 5,968,003 | A | 10/1999 | Sisson | 602/75 |
| 6,048,252 | A | 4/2000 | Sebring | 450/1 |
| 6,068,538 | A | 5/2000 | Alleyne | 450/58 |
| 6,086,450 | A | 7/2000 | Mankovitz | 450/20 |
| 6,168,498 | B1 | 1/2001 | Wagner | 450/58 |
| 6,361,397 | B1 | 3/2002 | Mankovitz et al. | 450/20 |
| 6,390,885 | B1 | 5/2002 | Brooks | 450/1 |
| 2002/0022433 | A1* | 2/2002 | Yeung et al. | 450/70 |

FOREIGN PATENT DOCUMENTS

| | | |
|---|---|---|
| FR | 002562768 A1 | 10/1985 |
| FR | 002702143 A1 | 9/1994 |
| WO | WO 95/05095 | 2/1995 |
| WO | WO 96/25131 | 8/1996 |

OTHER PUBLICATIONS www.tiac.net/users/fancyth/bustadjust.html, Mar. 4, 2002.
www.thetotalwomanboutique.com/html/body_the_choices_plus_bra.html, Mar. 4, 2002.
www.thetotalwomanboutique.com/html/body_the_sheer_comfort_bra.html, Mar. 4, 2002.
www.thetotalwomanboutique.com/html/body_the_freedom_lounge_bra.html, Mar. 4, 2002.
www.thetotalwomanboutique.com/html/body_the_comfort_plus_bra.html, Mar. 4, 2002.
www.thetotalwomanboutique.com/html/body_the_freedom_plus.html, Mar. 4, 2002.
www.thetotalwomanboutique.com/html/body_the_embrace_bra.html, Mar. 4, 2002.
www.reflectionsofsymmetry.com/reflections/brassier.html, Mar. 4, 2002.
www.jobst-usa.com/mamSupport.html, Jun. 25, 2002.

* cited by examiner

COMPRESSION GARMENT

CROSS-REFERENCE TO RELATED APPLICATION

This application is a continuation of U.S. application Ser. No. 10/187,164, filed Jul. 1, 2003, which is now U.S. Pat. No. 6,860,789, issued Mar. 1, 2005.

FIELD OF THE INVENTION

The present invention relates generally to the fields of compression garments and brassieres. More particularly, the present invention is directed to a garment for providing compressive forces to a human female torso so as to help eliminate or reduce swelling caused by an accumulation of lymph fluid in the torso region.

BACKGROUND OF THE INVENTION

The lymphatic system is a part of the human body's circulatory system. Through a complex network of lymph nodes and vessels, it transports and removes lymph fluid, which is a clear, high protein fluid, from the spaces between cells of the body. More specifically, the lymphatic system acts as a waste removal system for the body, removing metabolic wastes from the body's cells and then transporting that waste to the lymph nodes for filtering and detoxification. The "clean" lymph fluid is then returned to the bloodstream.

The lymphatic system, however, also serves as a conduit for cancerous cells to flow from a primary tumor to other sites. Consequently, lymph node biopsy is commonly used as a diagnostic procedure to determine the status of the cancer and to check to see if it has spread. Moreover, should the patient require surgery to remove cancerous sites, a surgeon may also have to remove lymph nodes and vessels from the affected area, such as the axilla (arm pit) and breast area in the case of breast cancer.

The removal of nodes and vessels in the affected area can compromise the local integrity of the lymphatic system, thereby adversely impacting lymphatic drainage. Radiation therapy can also damage or destroy lymphatic components, thereby further contributing to lymphatic compromise. The natural aging process may also contribute to lymphatic breakdown.

Impairment of the lymphatic system can radically reduce its capacity to transport, filter, and detoxify lymph fluid. It can also change the way that lymph fluid flows in that quadrant of the human body. Over time, sometimes years later, the lymph system can fail and fluid can back up, thereby causing swelling in a localized area. Greater fluid retention in the tissue also increases the risk that the patient will develop an infection, as one of the functions of the lymphatic system is to carry away and filter any bacteria that may be present in the lymph fluid.

Chronic swelling caused by the accumulation of lymph fluid in an area of the body is called lymphedema, a condition that is common among post-mastectomy patients and other cancer survivors who have had lymph nodes or vessels removed, or who have undergone radiation therapy. Lymphedema typically occurs in a limb (such as an arm), but it can also occur in the torso region, especially among breast cancer survivors. It may be characterized by swelling, heaviness, pain, pitting, tightness, or hardness of the tissues.

There are three stages of lymphedema, ranging from mild lymphedema, where the tissue may present with "pitting" (where the tissue, when pressed, will indent and hold the indention briefly) that is temporary and resolves overnight, to severe lymphedema (which is sometimes known as elephantitis), where the tissue increases in hardness or fibrosis and the swelling can be disfiguring and does not reverse itself. As with most medical conditions, it is desirable that lymphedema be diagnosed and treated as soon as possible, so as hopefully to prevent or at least retard progression of the condition from the mild to severe stages.

Treatment for lymphedema typically focuses on lymphatic drainage techniques and/or the use of compression garments, although proper skin care, exercise, and, where there is an infection, antibiotic therapy, can also be important components of a treatment plan. With lymphatic drainage techniques, which include "manual lymphatic drainage" and "simple lymphatic drainage," the patient or a therapist gently massages the connective tissue in specific directions in accordance with the structure and physiology of the lymphatic system, thereby stimulating the weakened system by pushing the stagnant fluid through the vessels. This also allows the venous system to reabsorb the fluid and helps establish channels through which lymph fluid can flow.

Compression garments may be used as an adjunct to, or as an alternative for, lymphatic drainage, depending on the severity of the condition. Compression garments are designed to apply external pressure to an affected area, thereby helping to maintain the size of that area so that swelling remains reduced. A compression garment can also improve the pumping of lymphatics and veins as well by creating a firm abutment for muscles to work against. Another benefit of a compression garment is that it reduces local blood volume in the veins, which in turn results in increased velocity in the vein and greater fluid throughput.

The most common types of compression garments are compression stockings or sleeves, which garments typically have to be expertly fit to the patient or, in some instances, custom made. Due to the complexities inherent in delivering the appropriate amounts of compression to various regions of the torso, however, few compression garments have been provided for use in the torso region, and even fewer exist that do not have to be custom made.

One such design is disclosed in U.S. Pat. No. 5,800,245 to Barbe-Vicuna et al. In this patent, Barbe-Vicuna et al. disclose a compression bra that uses a system of compression pads and cushions to increase pressure at certain desired locations on the torso, thereby purportedly facilitating and/or consolidating the benefits of manual lymphatic drainage. The disclosed garment, however, does not appear to deliver any overall compression to the torso beyond that of a typical brassiere. Instead, the Barbe-Vicuna et al. brassiere is limited to providing increased levels of compression at specific areas (namely, at the sites of the compression pads).

Another garment that is designed to provide compression to a wearer's breasts is disclosed in U.S. Pat. No. 5,839,942 to Miller. In this patent, Miller discloses a bra that is designed to treat post-partum engorgement, enlargement, and other conditions by delivering an adjustable level of compression, as well as by providing for the proper positioning of warm or cold compresses. The bra is fabricated from two layers of resilient material to provide compression and envelopment of the breasts. The overall design of this bra, however, would not be appropriate for the treatment of lymphedema, nor could it provide varying amounts of compression at different areas of the torso.

Finally, a large number of garments have been provided in the past that are designed to control breast motion (such as sports bras), provide invisible support under other garments (such as shelf bras), enhance the appearance of breasts (such as "push-up" bras), or some combination thereof (such as most "mainstream" bras). Examples of these garments are disclosed in U.S. Pat. Nos. 6,168,498; 4,440,174; and 5,868, 601 (among others), as well as in the references cited therein. None of these garments, however, disclose the garment of the claimed invention. Similarly, the garment disclosed in U.S. Pat. Nos. 6,086,450 and 6,361,397, which supposedly facilitate the drainage of lymphatic fluid from the breast area, are far removed from Applicant's design.

SUMMARY OF THE INVENTION

The present invention is directed to a garment for providing compressive forces to a torso to help eliminate or reduce swelling caused by any of a variety of reasons, including without limitation an accumulation of lymph fluid in the torso region.

One aspect of the invention is a brassiere comprising an outer covering and a front panel for providing compressive support to breast tissue. The front panel includes compression fabric and has an upper edge, a first side edge, a second side edge, and a lower edge. The front panel is attached to the outer covering at least at the first and second side edges. The front panel is moveable relative to said outer covering along a portion of said lower edge. The brassiere also includes a front shelf for providing upward compressive support to breast tissue. The front shelf is positioned proximate the lower edge of the front panel.

Another aspect of the present invention is a brassiere to be worn by a woman having axillae and an abdominal watershed, with the brassiere including an outer covering made from a compression fabric. The outer covering has a lower edge located about 1–8 cm above the woman's abdominal watershed when the brassiere is properly positioned on the woman. The brassiere also includes a pair of axilla gussets, each having upper edges located about 3.5–5 cm below a corresponding axilla when the brassiere is properly positioned on the woman.

Yet another aspect of the present invention is a brassiere having an outer cover made from a compression fabric having a modulus in the length dimension ranging from 0.5–1.5 pounds at 40% elongation and 1.0–2.0 pounds at 60% elongation, a modulus in the width dimension ranging from 0.2–1.0 pounds at 40% elongation and 0.5–1.6 pounds at 60% elongation, a stretch in the length dimension ranging from 160–220% and a stretch in the width dimension ranging from 120–170%. The brassiere also includes a front portion attached to said outer cover and including a compression fabric having a modulus in the length dimension ranging from 1.0–2.75 pounds at 30% elongation and 2.25–5.75 pounds at 60% elongation, a modulus in the width dimension ranging from 0.8–2.2 pounds at 40% elongation, a stretch in the length dimension ranging from 135–200% and a stretch in the width dimension ranging from 115–150%.

Still another aspect of the present invention is a brassiere to be worn by a woman having axillae, torso side regions and a breast region, with the brassiere including first and second axilla portions, each intended to be positioned proximate one of the axillae of the woman when the brassiere is properly worn. The first and second axilla portions provide a first level of compressive support. The brassiere also includes side portions intended to be positioned over the woman's torso side regions. The side portions provide more compressive support than the first level of compressive support. Also, the brassiere includes a front portion intended to be positioned over the woman's breast region. The front portion provides more compressive support than the side portions.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION OF THE INVENTION

The present invention is directed to a garment for providing compressive forces to a torso so as to help eliminate or reduce swelling caused by an accumulation of lymph fluid in the torso region. An example of the disclosed invention as designed for a human female torso is depicted schematically in FIGS. 1–5, although it should be understood that the present invention is not limited to this (or any other) particular embodiment, but rather is intended to cover all garments that fairly fall within the broad scope of the appended claims.

Figure 1:
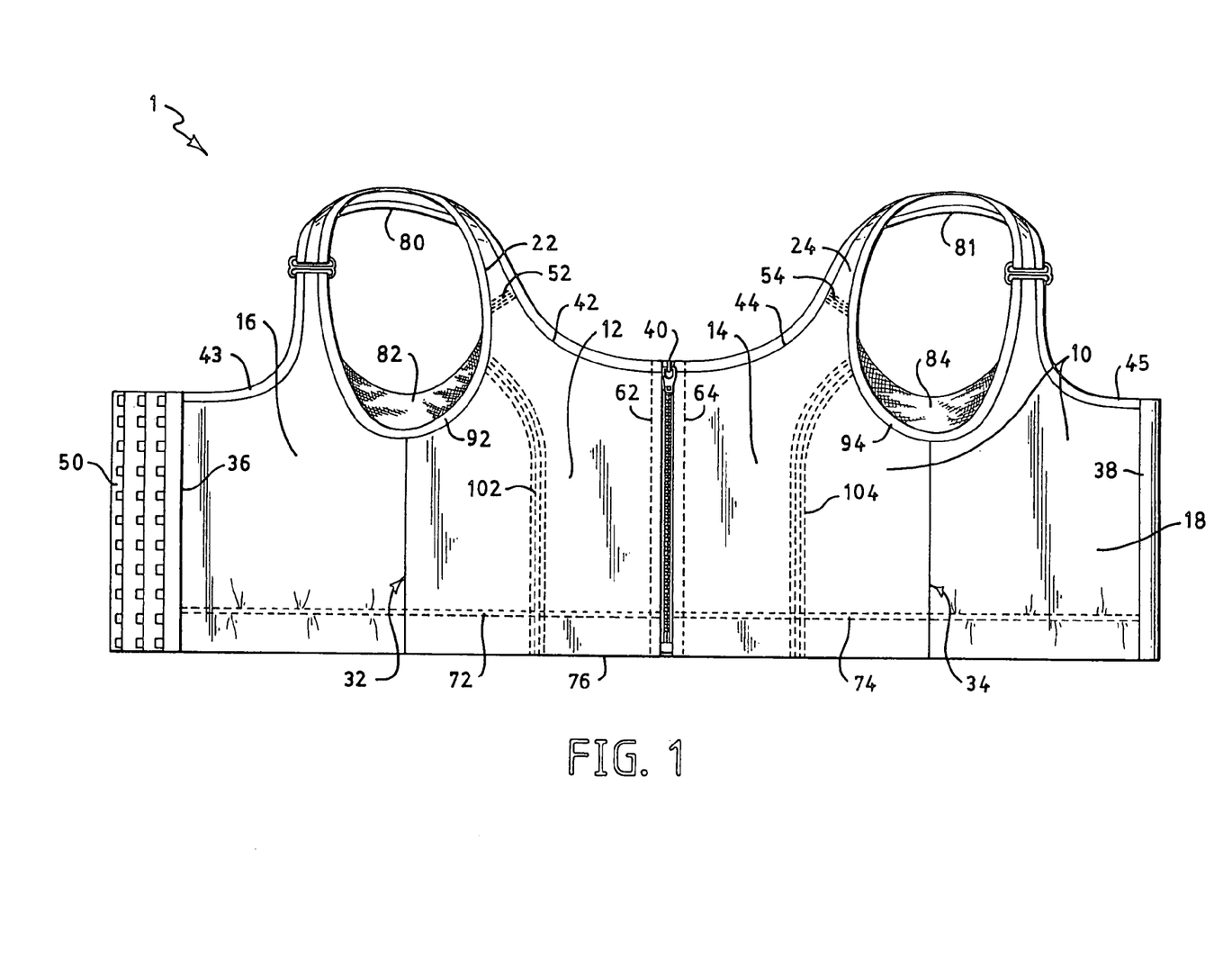
FIG. 1 is a plan view showing the outside of an embodiment of the compression garment of the present invention, with the garment being laid out flat for clarity of illustration.

Specifically with reference to FIG. 1, the disclosed compression garment 1 is shown laid out flat, with its outer covering 10 facing up. The outer covering 10 typically is made of a compression fabric, e.g., such as a LYCRA®-spandex blend and generally extends over the outer surface of the entire garment, thereby acting as a sort of unifying "skin" for the garment itself. The compression fabric used for outer covering 10 is selected so as to have a modulus (pounds of holding power) that is adequate to achieve the desired compression, while at the same time having a relatively large stretch. The material used in the construction of conventional bras is selected to adequately and comfortably support the breasts, but does so with little if any compression. As a related consequence, the fabric used in conventional bras has a substantially lower modulus than that used in the compression fabric for outer covering 10. By selecting a relatively high modulus-high stretch compression fabric for outer covering 10, garment 1 provides a relatively large amount of compression but does so with a relatively high degree of comfort.

As those skilled in the art will appreciate, the specific modulus and stretch for the compression fabric used for outer covering 10 is selected based on the specific application for which garment 1 is intended to be used. When garment 1 is intended to be used to control lymphedema, the modulus and the stretch for the compression fabric used for outer covering 10 will typically have the attributes listed below in Table 1:

TABLE 1

| Tester | Stretch performed with Zwick tester at 12 pounds effective load on 3rd cycle. |
|---|---|
| Modulus (pounds) | Length |
| | 40% elongation: 0.5–1.5 (typically 0.6–1.2) |
| | 60% elongation: 1.0–2.0 (typically 1.2–1.8) |
| | Width |
| | 40% elongation: 0.2–1.0 (typically 0.2–0.8) |
| | 60% elongation: 0.5–1.6 (typically 0.6–1.4) |
| Stretch | Length |
| | 160–220% (typically 170–210%) |
| | Width 120–170% (typically 125–165%) |
| Exemplary Material | 72% 40/34 T-285 Dull "Tactel" Nylon and 28% 70 T-162B bright LYCRA ® spandex |

The length dimension of the compression fabric is oriented in outer covering 10 so that it extends substantially parallel to the length (vertical) dimension of garment 1 when properly worn. The exemplary materials in Table 1 are just examples of suitable materials, and other materials satisfying the modulus and stretch characteristics listed in Table 1 are encompassed by the present invention. Subject to the desirability of having a relatively high extent of stretch along with a relatively high modulus, those skilled in the art will recognize that if garment 1 is intended for applications other than the control of lymphedema, the compression fabric used as outer cover 10 in the present invention may have attributes that vary somewhat from the parameters listed in Table 1. For aesthetic reasons, it generally is preferable that outer covering 10 be opaque. Also, the compression fabric used for outer cover 10 preferably has effective moisture management characteristics.

The outer covering 10 may be described as having front portions 12 and 14, which preferably can be connected to one another by a front closure 40 that permits the garment 1 to be donned or removed easily by a user with restricted mobility, such as a patient suffering from lymphedema or recovering from breast cancer surgery. While closure 40 is illustrated as a zipper in FIG. 1, the invention is not so limited. The present invention encompasses any closure that achieves the aforementioned function, including, without limitation, hook-and-loop closures such as VELCRO® closures, snaps and hook-and-eye closures. Outer covering 10 includes back portions 16 and 18, which preferably can be connected to one other by a rear closure 50 that is designed to offer maximum adjustability so as to permit a user to customize the amount of compressive forces that garment 1 provides and to adjust for fluctuations in breast size. Rear closure 50 is illustrated in FIG. 1 as a multi-position hook-and-eye fastener. The present invention, however, encompasses other fasteners than hook-and-eye fasteners as rear closure 50, including, without limitation, hook and-loop closures.

Shoulder strap 22 connects front portion 12 and back portion 16 and shoulder strap 24 connects front portion 14 and back portion 18. The shoulder straps 22 and 24 preferably are adjustable (such as with VELCRO® tabs), and are wider and more padded than regular brassiere straps, thus helping to redistribute breast and prosthesis weight as well as prevent the straps from digging into a user's shoulders. In this regard, the width of the shoulder straps 22 and 24 typically is about 2–5 cm (0.8–2 inches). Moreover, the design of the shoulder straps 22 and 24 is such that it helps minimize the amount of pressure at the wearer's "terminus" (an area halfway between the neck and the shoulder), which is a major lymphatic drainage area of the body.

Garment 1 typically includes side seams 32 and 34 positioned below the shoulder straps 22 and 24, respectively. For ease of reference, one may regard side seams 32 and 34 as delineating the front portions 12 and 14 of the outer covering 10 from the back portions 16 and 18, even though the fabric that comprises the outer covering 10 may be continuous across the side seams 32 and 34, rather than comprising separate pieces of fabric that are joined together. At the side seams 32 and 34, the outer covering 10 is typically joined to the inner layer(s) of compression fabric (discussed infra) and, if the outer covering is not continuous across the side seams 32 and 34, the front and back portions 12 and 16 and 14 and 18 may be joined to one another. In some cases, it may be desirable to omit the side seams 32 and 34.

Toward the lower edge of the garment 1, the outer covering 10 is preferably attached to a rib band 70 at lower seams 72 and 74. The rib band 70 typically is covered by the outer covering 10. This can be accomplished by either including another attachment seam at the lower edge 76, or wrapping a portion of the outer covering 10 around the lower edge 76 of the rib band 70 and attaching that portion of the outer covering 10 to the rib band 70 (and to the outer covering 10) at the lower seams 72 and 74. Preferably, the rib band 70 is made from an elastic material and is wide (such as is shown in FIG. 1), soft, and "non-rolling." Rib band 70 typically has a width in the range of 2.5–7.5 cm (1–3 inches).

In the arm holes defined by the shoulder straps 22 and 24, respectively, axilla gussets (or "underarm gussets") 82 and 84 are provided, respectively. Axilla gussets 82 and 84 are attached to the outer covering 10 at axilla seams 92 and 94. Each axilla gusset 82 and 84 is preferably comprised of a layer of low-compression or non-compression fabric that is breathable and provides for movement of the user's arms, with the fabric typically, but not necessarily, being made from a mesh or knit material. The axilla gussets 82 and 84 function so as to improve the wearability of the garment by preventing areas of flesh from overhanging the edges of the garment. Such overhanging flesh is a typical complaint associated with many prior art garments having axilla edges that only extend approximately to the region of the axilla seams 92 and 94 of the disclosed design, but no further. Thus, the material used for axilla gussets 82 and 84 is selected to provide only a limited amount of compression to the axillae region of the user.

The material used for axilla gussets 82 and 84 is not a "compression fabric" in the sense this term is used relative to outer covering 10. Suitable modulus and stretch attributes for the material used for axialla gussets 82 and 84 is listed below in Table 2:

TABLE 2

| Tester | Stretch and Modulus tests performed with Zwick tester at 15 pounds effective load on 5th cycle. |
|---|---|
| Modulus (pounds) | Length |
| | 60% elongation: 0.3–1.0 (typically 0.4–0.85) |
| | 80% elongation: 0.7–1.8 (typically 0.8–1.65) |
| | Width |
| | 40% elongation: 0.65–1.7 (typically 0.75–1.55) |
| Stretch | Length |
| | 150–200% (typically 157–193%) |
| | Width |
| | 75–115% (typically 85–105%) |

TABLE 2-continued

| | |
|---|---|
| Exemplary Material | 84.33% 50/34 Semi-Dull Polyester and 15.67% 40 T-162B bright LYCRA ® |

The length dimension of the fabric of Table 2 is oriented in axilla gussets 82 and 84 so that it extends substantially parallel to the length (vertical) dimension of garment 1 when properly worn. The exemplary materials in Table 2 are just examples of suitable materials, and other materials satisfying the modulus and stretch characteristics listed in Table 2 are encompassed by the present invention.

Figure 2:
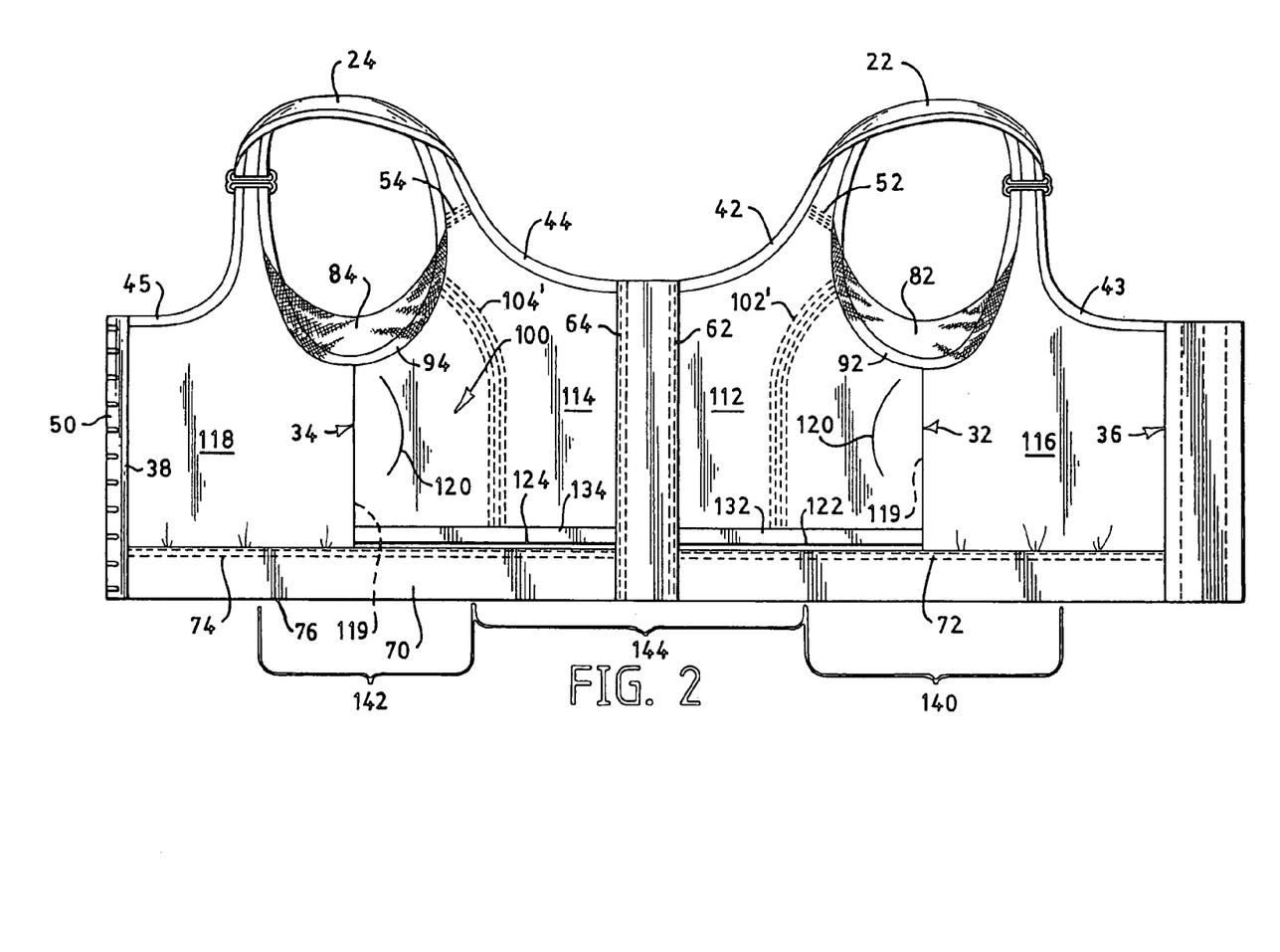
FIG. 2 is a plan view showing the inside of the embodiment depicted in FIG. 1.

With reference to FIG. 2, the inside of the compression garment 1 is shown, with the garment again being laid out flat. As will be described more fully, the inside of the compression garment 1, which is the side that contacts the user's skin, is generally covered with one or more layers of a compression fabric that forms liner 100, which contains elastic, e.g., spandex fibers. In comparison to the compression fabric used to form the outer covering 10, the compression fabric used for liner 100 is typically lighter weight, and preferably should be soft as it is designed to contact the user's skin. In addition, the compression fabric for liner 100 generally has a higher modulus than the compression fabric used for the outer covering 10 and typically has less stretch, thereby avoiding a situation wherein the outer covering 10 stretches less than that of the inner layer(s), which could inhibit the function of the inner layer(s). Further, the compression fabric for liner 100 generally has good moisture management attributes, and is relatively breathable. The compression fabric for liner 100 may have a mesh construction, although non-mesh materials that have the desired breathability, softness, and stretch may also be used.

Suitable modulus and stretch attributes for compression fabric used for liner 100 are identified below in Table 3:

TABLE 3

| | |
|---|---|
| Tester | Stretch and modulus test performed with Zwick tester at 30 pounds effective load on 3$^{rd}$ cycle. |
| Modulus (pounds) | Length 30% elongation: 1.0–2.75 (typically 1.15–2.5) 60% elongation: 2.25–5.75 (typically 2.70–5.45) Width 40% elongation: 0.8–2.2 (typically 1.0–2.0) |
| Stretch | Length 135–200% (typically 150–183%) Width 115–150% (typically 120–145%) |
| Exemplary Material | 72% 40/34 T-285 Semi-Dull "Tactel" Nylon and 28% 280 T-127 Dull LYCRA ® |

The length dimension of the fabric of Table 3 is oriented in liner 100 so that it extends substantially parallel to the length (vertical) dimension of garment 1 when properly worn. The exemplary materials in Table 3 are just examples of suitable materials, and other materials satisfying the modulus and stretch characteristics listed in Table 3 are encompassed by the present invention.

It is generally desirable to join the outer covering 10 to liner 100 at least along a portion of the top seams 42–45, the shoulder seams 52 and 54, and the center seams 62 and 64. Moreover, the outer covering 10 is also preferably not attached to the liner 100 along princess seams 102 and 104 in the outer covering and princess seams 102' and 104' in the liner, the function of which will be described more fully infra.

For ease of reference, it may be helpful to refer to liner 100 as being divided up into multiple "panels," although use of such terminology is not meant to imply that a continuous piece of fabric could not extend across multiple panels. Thus, one could describe liner 100 as comprising two front panels 112 and 114 of compression fabric, each of which extends from a side seam 32 or 34 to a front seam 62 or 64, and two back panels 116 and 118 of the compression fabric, each of which extends from a side seam 32 or 34 to a back seam 36 or 38. Alternately, one could refer to the entire front region (from side seam 32 to side seam 34, passing through zipper 40) and the entire back region (from side seam 34 to side seam 32, passing through fasteners 50) as separate front and back "panels," respectively. In the present description of the invention, however, only the former nomenclature will be used. Where appropriate, though, either or both nomenclatures may be applicable to the claims.

Front panels 112 and 114 preferably are attached to the outer covering 10 at side seams 32 and 34, axilla seams 92 and 94, shoulder seams 52 and 54, top seams 42 and 44, and center seams 62 and 64. Preferably, each front panel 112 and 114 is comprised of two or more layers of compression fabric, although it would be possible to use a single layer of fabric if such fabric provided the proper amount of compression and stretch. Each front panel 112 and 114 may also contain a region 119 between the layers of fabric (or a separate pocket) that is accessible from an area near side seams 32 or 34 for receiving a breast prosthesis (not shown), such as is often used by users who have had some or most of their breast tissue removed during breast cancer surgery. In this regard, an opening 120 in communication with region 119 may be provided in front panels 112 and 114, typically adjacent the side seams 32 and 34, but also positionable elsewhere on the front panels.

Front panels 112 and 114 preferably are moveable relative to, and typically not attached to, the outer covering 10 along lower edges 122 and 124. Moreover, the portions of the front panels 112 and 114 near the lower edges 122 and 124 preferably are formed into two front "shelves" (or integral "shelf bras") 132 and 134 for providing upward compressive support to the breast tissue, as will be described in detail infra. The front shelves 132 and 134, however, preferably do not extend past the side seams 32 and 34 so as to avoid producing an adverse "cutting" effect in the inferior axillae region.

Back panels 116 and 118 generally are attached to the outer covering 10 along each side of the panel, such as at side seams 32 and 34, axilla seams 92 and 94, top seams 43 and 45, back seams 36 and 38, and lower seams 72 and 74. Like the front panels 112 and 114, the back panels 116 and 118 are also preferably made from a fabric having the breathability, softness and stretchability attributes discussed above relative to compression fabric 100. However, as explained infra, it is generally desirable that the back panels 116 and 118 provide less compressive force to the back of the user's torso than the front panels 112 and 114 provide to the front. This can be achieved by providing only one layer of compression fabric in the portion of liner 100 making up the back panels 116 and 118, although the use of additional layers falls within the scope of the disclosed invention. Alternatively, lesser amounts of compression may be achieved with back panels 116 and 118 by constructing the panels with different materials and/or designs (e.g., stitching) than that used for panels 112 and 114 so as to achieve the lesser amounts of compression.

Figure 3:
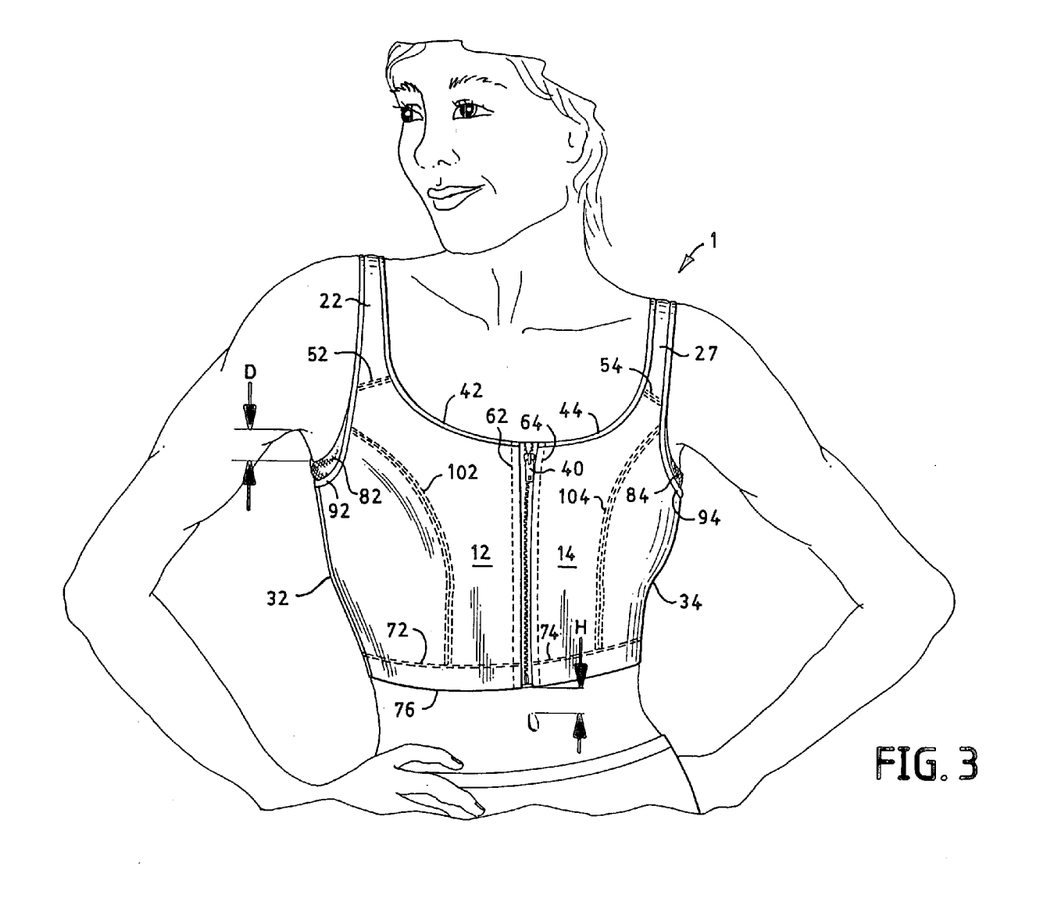
FIG. 3 is a front perspective view of the embodiment depicted in FIG. 1 as it may look when being worn by a human female.
Figure 4:
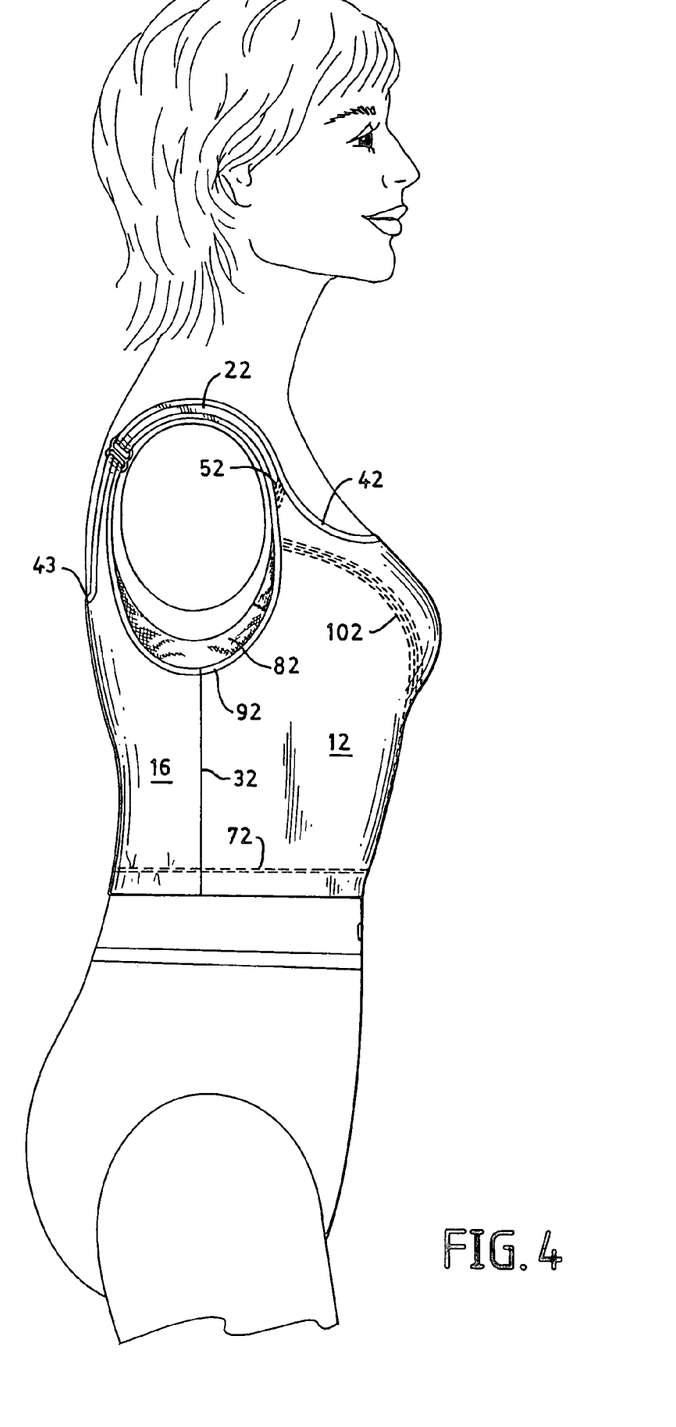
FIG. 4 is a side perspective view of the embodiment depicted in FIG. 1 as it may look when being worn by a human female.
Figure 5:
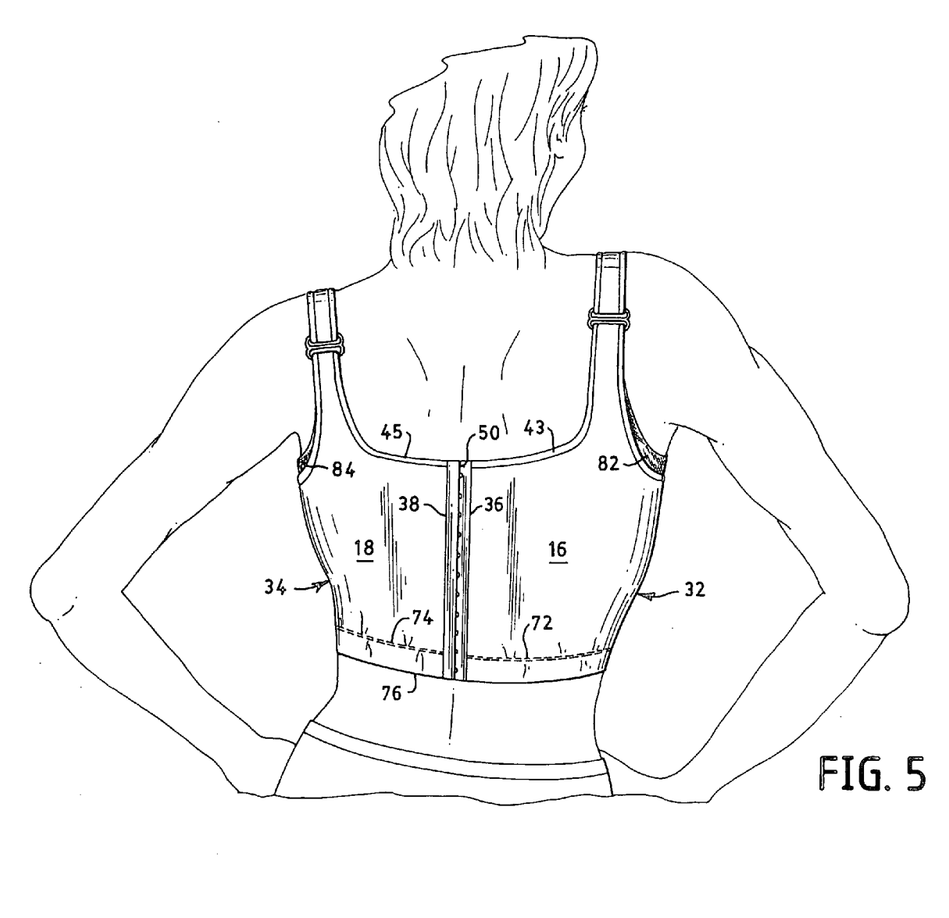
FIG. 5 is a rear perspective view of the embodiment depicted in FIG. 1 as it may look when being worn by a human female.

With reference to FIGS. 3–5, the proper positioning of the disclosed compression garment and its function in providing compressive forces to a human female torso will now be described.

As may be seen in FIGS. 3–5, the garment 1 is designed to be worn by a user in much the same manner as a typical brassiere. The garment 1, however, preferably is designed and fitted so that the top edge of each axilla gusset 82 and 84 extends about 5 cm (2 inches) above a standard bra silhouette, and thus falls between approximately 3.5–5 cm (about 1.5–2.0 inches) below the corresponding one of the user's axilla. This distance, noted in FIG. 3 as distance D, is measured between the top edge of an axilla gusset 82, 84 and the portion of the axilla defined by an imaginary straight edge that just touches front and back portions of the axilla when the arm is positioned on the hip of a user, as shown in FIG. 3. In other words, the upper-most extent of distance D does not extend up into the base or inner-most part of the axilla, but rather extends to just that portion touched by the previously mentioned straight edge. Similarly, it is preferable that the lower edge 76 of the garment 1 extends to about the inferior rib cage on the side of the user's trunk, and to approximately 1–8 cm (0.5–3 inches) above the user's naval in the front (a height noted in FIG. 3 as H), an area referred to as the "abdominal watershed." Typically, but not necessarily, height H will range from 1.5–5 cm (0.6–2 inches). The back of the garment 1, shown in FIG. 5, and hence closure 50, preferably extends from the user's waist region (at the lower edge 76), at about the same height as the portion of the edge 76 adjacent closure 40, to a point that falls within an area defined by the user's fifth and eighth thoracic vertebrae (T5–T8) (at the top edges 43 and 45). In other words, the lower edge 76 is substantially coextensive with an imaginary horizontal plane intersecting the user and located a distance H (FIG. 3) above the user's navel.

Like all of the preferred features of the disclosed embodiment, the preferred positioning described above is not essential to the present invention, but rather is designed to avoid potentially sensitive post-surgical sites and to avoid impeding the natural flow of lymphatic fluid in the body. In addition, this preferred positioning helps ensure that the compressive support provided by the garment is directed to those areas where the support will be most effective. The non-rolling rib band 70 generally helps anchor garment 1 in this preferred positioning.

The compressive forces provided to the torso or the user by the garment 1 generally are provided by the layer(s) of compressive fabric in liner 100. The outer covering 10, however, may also contribute to the compressive effect, as well as provide stability to the garment and support for the inner layer(s). By design, the amount of compressive support generally provided by any particular region of the garment 1 varies due to different fabric used in those areas, as well as the type and disposition of the stitching used to secure the fabrics together. The amount of compression applied by garment 1 will also vary as a function of the fit point selected by the designer of the garment. The various fabric attributes listed above in Tables 1 and 3 were selected for a fit point at a stretch of about 20%. Those skilled in the art will appreciate that at a different fit point, somewhat different attributes for the compression fabric used in garment 1 may be desirable.

Figure 6:
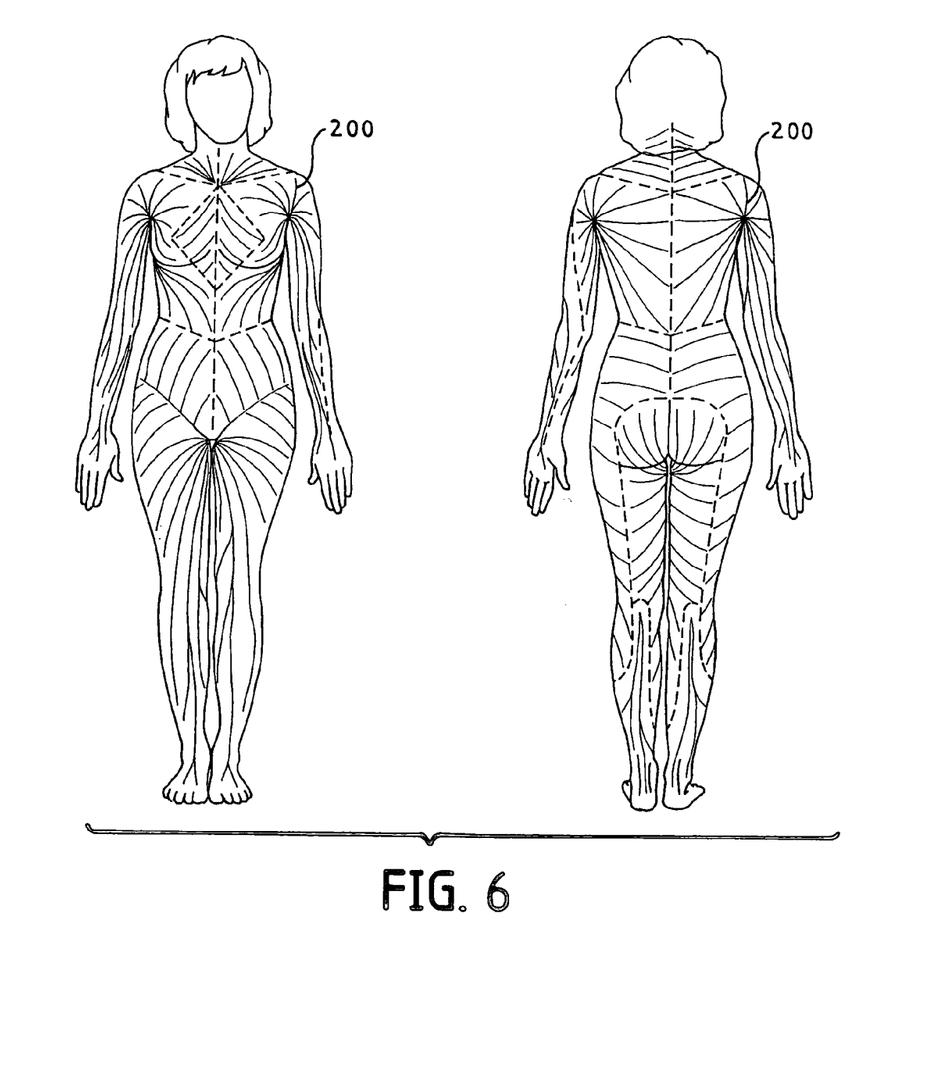
FIG. 6 is a diagram showing a typical person's superficial lymphatic drainage pathways.

The least amount of compressive support, which shall be designated a "first level" of support, is provided by the axilla gussets 82 and 84, which, as noted above, are preferably fabricated from a single layer that provides little compression. The term "level," as used in the description of the invention and in the claims, refers to a range of support, and not a single numerically quantified amount of support. The level of support may vary, from location to location, within the portion of garment 1 under consideration (e.g., within axilla gussets 82 and 84), and also is intended to encompass a range of average support across the entire portion. As may be seen in FIG. 6, which is a diagram showing a typical person's superficial lymphatic drainage pathways, the axillae 200 serve as critical collection and drainage points for the lymphatic system. Thus, while some level of compression in this area is desirable, care should be taken so as to not cut into and restrict lymphatic drainage through this region.

The next level of compressive support, or the "second level" of support, generally is provided by the single layer of compressive fabric 100 in the back panels 116 and 118, which, as noted above, act in combination with the outer covering 10. As one skilled in the art will readily appreciate, of course, the amount of compressive support provided by the back panels 116 and 118 is not uniform over each panel, but rather tends to increase the closer one gets to a rigid seam, such as side seams 32 and 34 and back seams 36 and 38. Indeed, as discussed below, the area on both sides of the side seams 32 and 34 may more properly be referred to as providing a "third level" of support. Nonetheless, the average amount of compression provided over the back regions from an area beginning approximately half way across each back panel 116 and 118 and extending across the rear closure 50 is generally greater than the amount of compression provided in the axillae regions and is less than the average amount of compression provided in the front and side regions (as discussed below), thus resulting in the "second level" designation. Having less compressive force in this region in comparison to the amount of compression provided in the front or sides is generally desirable because it permits the ribs to expand, allowing ease of breathing, rather than constantly being in a state of significant compression.

The next highest level of compressive support, or the "third level" of support, generally is provided over the user's side region, beginning at an area that for the right side (shown in FIG. 4) begins at approximately one-third of the distance between seam 32 and seam 62, as measured horizontally moving from seam 32 toward seam 62, and continues over the side seam 32 to an area approximately half way between the side seam 32 and the back seam 36. This area is identified by bracket 140 in FIG. 2. It is desirable to provide a greater amount of compression support here than in the regions of first or second level of support because lymphatic fluid tends to back up in the inferior axillae region. Thus, in a user with a compromised or impaired lymphatic drainage system, the amount of pressure in the drainage system is greater in this region, therefore necessitating a greater degree of compression so as to maintain the size of the affected area, reduce local blood volume, and improve system efficiency by creating a firm abutment against which muscles can work. Such "third level" of support is also provided in the portion of the garment 1 covering the user's left side, as indicated by bracket 142 in FIG. 2.

The greatest level of compressive support, or the "fourth level" of support, generally is provided over the user's breast region. This region, identified by bracket 144 in FIG. 2, extends from the outside edge of the user's right breast (about 2.5–3.5 cm or 1–1.5 inches outwardly of princess seam 102'), across the closure 40, and terminating near the outside edge of the user's left breast (about 2.5–3.5 cm or 1 inch to 1.5 inches outwardly of the princess seam 104'). The exact area where the "fourth level" of support transitions to the "third level" will depend on the geometry of the user, and, more particularly, on the user's breast size. It is preferable that compression in the breast region be the greatest because this region typically is most compromised during cancer treatments, thereby increasing the likelihood and severity of localized swelling.

The princess seams 102 and 104 and the front shelves 132 and 134 are two of the elements of the disclosed design that help enable the front panels 116 and 118 of the garment to provide, in combination with the outer covering 10, the fourth level of support to the user's breast region, although other combinations of elements may be used.

More specifically, the princess seams 102 and 104 in outer covering 10, and the princess seams 102' and 104' in liner 100, create convex contours in the front panels 116 and 118 that enable the panels to encapsulate and hold the user's breasts in place at the same time that the combination of the compression fabric and the outer covering 10 compresses the breast tissue in toward the torso on all sides. By comparison, a standard bra "cup" only encapsulates breast tissue; it does not necessarily provide for or facilitate compression.

Meanwhile, the two front shelves 132 and 134 of the front panels 116 and 118 act as "floating bras" and likewise help encapsulate and compress the user's breast tissue. In particular, the front shelves 132 and 134 provide upward support to the breast tissue as well as vertical compression that, if separately measured, is believed to be approximately a "second level" of support. Without the use of the shelves 132 and 134 (or an acceptable alternative), the user's breasts would hang down somewhat and thus would be out of alignment when compressed by front panels 116 and 118. With the shelves 132 and 134, however, the breast tissue is held in a proper neutral position so that inward compressive forces acting on the tissue provide maximum effect. While the use of shelves 132 and 134 is generally desirable, in some cases is may be desirable to omit the shelves.

Through the use of the present invention, a user can obtain the proper amount of compression that is required for each area of the torso. Moreover, the multi-position closure 50 on the back enables the user to increase or decrease the total amount of compression provided by the garment 1 (such as when the size of the user's breasts increases or decreases), while still maintaining the proper proportionality among the various regions. With a typical brassiere, a user who sought to increase the amount of compression in one region, such as by making the garment tighter in back, risked applying too much compression in a more sensitive region and thereby creating adverse consequences, such as the unwanted restriction of fluid flow.

The present invention seeks to avoid these shortcomings in the prior art, and provides an adjustable compression garment that can be mass-produced rather than having to be custom fit. In the present application, however, only a preferred embodiment of the present invention has been disclosed and discussed, and it should be understood that the present invention is not limited to this (or any other) particular embodiment. On the contrary, the present invention is intended to cover all alternatives, modifications and equivalents that may be included within the spirit and scope of the appended claims.

What is claimed is:

1. A brassiere comprising:
   a. an outer covering;
   b. a front panel for providing compressive support to breast tissue, said front panel including compression fabric and having an upper edge, a first side edge, a second side edge, and a lower edge, and wherein said front panel is attached to said outer covering at least at said first and second side edges, further wherein said front panel is moveable relative to said outer covering along a portion of said lower edge; and
   c. a front shelf for providing upward compressive support to breast tissue, said front shelf being positioned proximate said lower edge of said front panel, wherein said compression fabric included in said front panel has a modulus in the length dimension ranging from 1.0–2.75 pounds at 30% elongation and 2.25–5.75 pounds at 60% elongation and a modulus in the width dimension ranging from 0.8–2.2 pounds at 40% elongation.

2. A brassiere of claim 1, further comprising a back panel attached to said outer covering at said first and second side edges.

3. A brassiere of claim 2, wherein said front shelf extends along said lower edge of said front panel from approximately said first side edge of said front panel to approximately said second side edge of said front panel.

4. A brassiere of claim 1, wherein said outer covering includes compression fabric.

5. A brassiere of claim 1, wherein said compression fabric included in said front panel has a modulus in the length dimension ranging from 1.15–2.5 pounds at 30% elongation and 2.7–5.45 pounds at 60% elongation, a modulus in the width dimension ranging from 1.0–2.0 pounds at 40% elongation, a stretch in the length dimension ranging from 150–183% and a stretch in the width dimension ranging from 120–145%.

6. A brassiere of claim 1, wherein said compression fabric included in said front panel has a stretch in the length dimension ranging from 135–200% and a stretch in the width dimension ranging from 115–150%.

7. A brassiere of claim 1, wherein said outer covering includes compression fabric having a modulus in the length dimension ranging from 0.5–1.5 pounds at 40% elongation and 1.0–2.0 pounds at 60% elongation, a modulus in the width dimension ranging from 0.2–1.0 pounds at 40% elongation and 0.5–1.6 pounds at 60% elongation, a stretch in the length dimension ranging from 160–220% and a stretch in the width dimension ranging from 120–170%.

8. A brassiere according to claim 1, further including at least two princess seams in said outer covering.

9. A brassiere according to claim 2, wherein said back panel has an adjustable closure for permitting a user to adjust the size of the brassiere.

10. A brassiere according to claim 1, further including at least two princess seams in said front panel.

11. A brassiere according to claim 1, wherein said front panel is configured to be between said outer covering and a wearer's body.

12. A garment for providing compressive forces to a torso, the garment comprising:
    a. an outer covering of compression fabric, including front and back portions;
    b. one or more shoulder straps for connecting said front portion of said outer covering to said back portion of said outer covering;
    c. a front panel for providing compressive support to at least a portion of the front of the torso, said front panel including at least one layer of compression fabric and having an upper edge, a first side edge, a second side edge, and a lower edge, and wherein said front panel is attached to said outer covering at least at said first and second side edges, and wherein said front panel is moveable relative to said front portion of said outer covering along a portion of said lower edge;

d. a front shelf for providing upward compressive support to breast tissue, said front shelf being positioned near said lower edge of said front panel; and e. a back panel for providing compressive support to at least a portion of the back of the torso, said back panel including at least one layer of compression fabric and having a first side edge and a second side edge, and wherein said back panel is attached to said outer covering at said first and second side edges, wherein said at least one layer of compression fabric for said front panel has a modulus in the length dimension ranging from 1.0–2.75 pounds 430% elongation and 2.25–5.75 pounds at 60% elongation and a modulus in the width dimension ranging from 0.8–2.2 pounds at 40% elongation.

13. A garment of claim 12, wherein said at least one layer of compression fabric in said front panel includes at least two layers of compression fabric.

14. A garment of claim 12, wherein said outer covering includes a first side seam and a second side seam, further wherein said first side edge of said front panel is attached to said first side seam and said second side edge of said front panel is attached to said second side seam.

15. A garment of claim 12, wherein said at least one layer of compression fabric for said front panel has a stretch in the length dimension ranging from 135–200% and a stretch in the width dimension ranging from 115–150%.

16. A garment of claim 12, wherein said compression fabric for said outer covering has a modulus in the length dimension ranging from 0.5–1.5 pounds at 40% elongation and 1.0–2.0 pounds at 60% elongation, a modulus in the width dimension ranging from 0.2–1.0 pounds at 40% elongation and 0.5–1.6 pounds at 60% elongation, a stretch in the length dimension ranging from 160–220% and a stretch in the width dimension ranging from 120–170%.

17. A garment of claim 12, further including at least two princess seams in said outer covering.

18. A garment of claim 13, wherein said at least two layers of compression fabric included in said front panel are attached to one another.

19. A garment of claim 12, further comprising a pair of axilla gussets for retaining tissue near a wearer's axillae, each of said pair of axilla gussets having a top edge and wherein the distance between said top edge and the wearer's axilla when said garment is properly positioned on the wearer is approximately 3.5–5 cm.

20. A garment of claim 12, wherein said garment is designed to be worn by a human female and wherein said garment is sized so that the distance H between said lower edge of said front panel and the wearer's navel when said garment is properly positioned on the wearer is approximately 1–8 cm.

21. A garment of claim 20, wherein said distance H ranges from 1.5–5 cm.

22. A garment of claim 12, further including at least two princess seams in said front panel.

23. A brassiere to be worn by a woman having axillae and an abdominal watershed, the brassiere comprising:

a. an outer covering made from a compression fabric, said outer covering having a lower edge located about 1–8 cm above the woman's abdominal watershed when the brassiere is properly positioned on the woman, said compression fabric having a modulus in the lenath dimension ranging from 0.5–1.5 pounds at 40% elongation and 1.0–2.0 pounds at 60% elongation, a modulus in the width dimension ranging from 0.2–1.0 pounds at 40% elongation and 0.5–1.6 pounds at 60% elongation, a stretch in the length dimension ranging from 160–220% and a stretch in the width dimension ranging from 120–170%; and b. a pair of axilla gussets, each having upper edges located about 3.5–5 cm below a corresponding axilla when the brassiere is properly positioned on the woman.

24. A brassiere according to claim 23, further including a rear closure sized to extend between said lower edge and a position in a range defined by the woman's fifth and eighth thoracic vertebrae, when the brassiere is properly positioned on the woman.

25. A brassiere according to claim 23, further including a front shelf for providing upward compressive support to breast tissue of the woman.

26. A brassiere according to claim 23, wherein said lower edge is located about 1.5–5 cm above the woman's abdominal watershed when the brassiere is properly positioned on the woman.

27. A brassiere to be worn by a woman having axillae, torso side regions and a breast region, the brassiere comprising:

a. first and second axilla portions, each intended to be positioned proximate one of the axillae of the woman when the brassiere is properly worn, said first and second axilla portions providing a first level of compressive supptrt;

b. a back portion intended to be positioned over the woman's back region, said back portion providing a second level of compressive support that is greater than said first level of compressive support;

c. side portions intended to be positioned over the woman's torso side regions, said side portions providing more compressive support than said second level of compressive support; and d. a front portion intended to be positioned over the woman's breast region, said front portion providing more compressive support than said side portions.

28. A brassiere according to claim 27, wherein said front portion includes a front shelf for providing compressive support to breast tissue of the woman.

29. A brassiere according to claim 27, wherein at least said side portions and said front portion are made from compression fabric.

30. A brassiere to be worn by a woman having an abdominal watershed and thoracic vertebrae, the bra comprising:

a. an outer covering made from a compression fabric, said outer covering having a lower edge, wherein said outer covering is sized so that when said brassiere is properly positioned on the woman said lower edge is positioned about 1–8 cm above the woman's abdominal watershed, wherein said compression fabric has a modulas in the length dimension ranging from 0.5–1.5 pounds at 40% elongation and 1.0–2.0 pounds at 60% elongation, a modulus in the width dimension ranging from 0.2–1.0 pounds at 40% elongation and 0.5–1.6 pounds at 60% elongation, a stretch in the length dimension ranging from 160–220% and a stretch in the width dimension ranging from 120–170%;

b. a rear closure sized to extend between said lower edge and a position in a range defined by the woman's fifth and eighth thoracic vertebrae, when the brassiere is properly positioned on the woman; and c. a front closure.

31. A brassiere according to claim 30, further including a front panel having a front shelf for providing compressive support to breast tissue of the woman.

32. A brassiere according to claim 30, wherein said lower edge is positioned about 1.5–5 cm above the woman's abdominal watershed when the brassiere is properly positioned on the woman.

33. A brassiere according to claim 31, wherein said front panel is made from a compression fabric having a modulus in the length dimension ranging from 1.0–2.75 pounds at 30% elongation and 2.25–5.75 pounds at 60% elongation, a modulus in the width dimension ranging from 0.8–2.2 pounds at 40% elongation, a stretch in the length dimension ranging from 135–200% and a stretch in the width dimension ranging from 115–150%.

34. A brassiere, comprising:
   a. an outer cover made from a compression fabric having a modulus in the length dimension ranging from 0.5–1.5 pounds at 40% elongation and 1.0–2.0 pounds at 60% elongation, a modulus in the width dimension ranging from 0.2–1.0 pounds at 40% elongation and 0.5–1.6 pounds at 60% elongation, a stretch in the length dimension ranging from 160–220% and a stretch in the width dimension ranging from 120–170%; and
   b. a front portion attached to said outer cover and including a compression fabric having a modulus in the length dimension ranging from 1.0–2.75 pounds at 30% elongation and 2.25–5.75 pounds at 60% elongation, a modulus in the width dimension ranging from 0.8–2.2 pounds at 40% elongation, a stretch in the length dimension ranging from 135–200% and a stretch in the width dimension ranging from 115–150%.

35. A brassiere according to claim 34, further including a front shelf for providing compressive support to breast tissue of a user.

36. A brassiere according to claim 34, wherein said outer cover further includes:
   a. a lower edge that is positioned about 1–8 cm above a user's abdominal watershed when the brassiere is properly worn; and
   b. a rear closure sized to extend between said lower edge and a position in a range defined by the fifth and eighth thoracic vertebrae of the wearer of the brassiere, when the brassiere is properly worn.

37. A brassiere comprising:
   a. an outer covering;
   b. a front panel for providing compressive support to breast tissue, said front panel including compression fabric and having an upper edge, a first side edge, a second side edge, and a lower edge, and wherein said front panel is attached to said outer covering at least at said first and second side edges, further wherein said front panel is moveable relative to said outer covering along a portion of said lower edge; and
   c. a front shelf for providing upward compressive support to breast tissue, said front shelf being positioned proximate said lower edge of said front panel,
   d. a pair of axilla gussets for retaining tissue near a wearer's axillae, each of said pair of axilla gussets having a top edge and wherein the distance between said top edge and the wearer's axilla when said garment is properly positioned on the wearer is approximately 3.5–5 cm.

38. A brassiere according to claim 37, further comprising a back panel attached to said outer covering at said first and second side edges.

39. A brassiere according to claim 38, wherein said front shelf extends along said lower edge of said front panel from approximately said first side edge of said front panel to approximately said second side edge of said front panel.

40. A brassiere according to claim 37, wherein said outer covering includes compression fabric.

41. A brassiere according to claim 37, wherein said compression fabric included in said front panel has a modulus in the length dimension ranging from 1.0–2.75 pounds at 30% elongation and 2.25–5.75 pounds at 60% elongation, a modulus in the width dimension ranging from 0.8–2.2 pounds at 40% elongation, a stretch in the length dimension ranging from 135–200% and a stretch in the width dimension ranging from 115–150%.

42. A brassiere according to claim 37, wherein said compression fabric included in said front panel has a modulus in the length dimension ranging from 1.15–2.5 pounds at 30% elongation and 2.7–5.45 pounds at 60% elongation, a modulus in the width dimension ranging from 1.0–2.0 pounds at 40% elongation, a stretch in the length dimension ranging from 150–183% and a stretch in the width dimension ranging from 120–145%.

43. A brassiere according to claim 37, wherein said compression fabric included in said front panel has a stretch in the length dimension ranging from 135–200% and a stretch in the width dimension ranging from 115–150%.

44. A brassiere according to claim 37, wherein said compression fabric included in said front panel has a modulus in the length dimension of 1.0–2.75 pounds at 30% elongation and 2.25–5.75 pounds at 60% elongation and a modulus in the width dimension of 0.8–2.2 pounds at 40% elongation.

45. A brassiere according to claim 40, wherein said outer covering includes compression fabric having a modulus in the length dimension ranging from 0.5–1.5 pounds at 40% elongation and 1.0–2.0 pounds at 60% elongation, a modulus in the width dimension ranging from 0.2–1.0 pounds at 40% elongation and 0.5–1.6 pounds at 60% elongation, a stretch in the length dimension ranging from 160–220% and a stretch in the width dimension ranging from 120–170%.

46. A brassiere according to claim 37, further including at least two princess seams in said outer covering.

47. A brassiere according to claim 38, wherein said back panel has an adjustable closure for permitting a user to adjust the size of the brassiere.

* * * * *

UNITED STATES PATENT AND TRADEMARK OFFICE
CERTIFICATE OF CORRECTION

| | | |
|---|---|---|
| PATENT NO. | : 7,144,294 B2 | Page 1 of 1 |
| APPLICATION NO. | : 11/200214 | |
| DATED | : December 5, 2006 | |
| INVENTOR(S) | : Lesli R. Bell and Eugenie Z. Lindahl | |

It is certified that error appears in the above-identified patent and that said Letters Patent is hereby corrected as shown below:

In claim 23, column 13, line 66, delete "lenath" and insert -- length -- therefor.

In claim 30, column 14, line 55, delete "modulas" and insert -- modulus -- therefor.

Signed and Sealed this

Twenty-second Day of May, 2007

JON W. DUDAS
*Director of the United States Patent and Trademark Office*